United States Patent
Bristow

(10) Patent No.: US 9,872,498 B2
(45) Date of Patent: Jan. 23, 2018

(54) PROCESS FOR PREPARING A NOVEL FORMULATION OF RIMSULFURON AND USE OF THE SAME

(71) Applicant: Rotam Agrochem International Company Limited, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/620,477

(22) Filed: Feb. 12, 2015

(65) Prior Publication Data

US 2016/0235066 A1     Aug. 18, 2016

(51) Int. Cl.
*A01N 25/32* (2006.01)
*A01N 43/54* (2006.01)
*A01N 47/36* (2006.01)

(52) U.S. Cl.
CPC .................................. *A01N 47/36* (2013.01)

(58) Field of Classification Search
None
See application file for complete search history.

(56) References Cited

U.S. PATENT DOCUMENTS

| | | | |
|---|---|---|---|
| 5,516,750 A | 5/1996 | Willms et al. | |
| 8,754,010 B2* | 6/2014 | Zagar | A01N 47/36 504/130 |
| 8,809,535 B2* | 8/2014 | Witschel | A01N 43/90 504/246 |

FOREIGN PATENT DOCUMENTS

| | | | |
|---|---|---|---|
| CN | 104041506 | * | 9/2014 |
| CN | 103719127 | * | 4/2016 |

OTHER PUBLICATIONS

Bu Hai-Yan et al., Advances on degradation behavior of rimsulfuron in environment, Applied Chemical Industry, Nov. 28, 2006, vol. 35, No. 11, section 3.2.

* cited by examiner

*Primary Examiner* — Alton Pryor
(74) *Attorney, Agent, or Firm* — Dickinson Wright PLLC

(57) ABSTRACT

A herbicidal composition including rimsulfuron with anti-hydrolysis agent, wherein the anti-hydrolysis agent is 2-isoxazoline-3-carboxylic acid derivatives having formula (I):

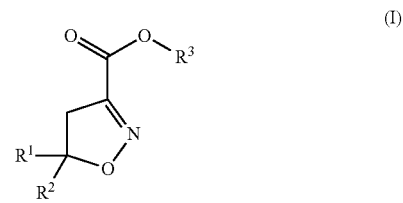

in which
$R^1$ is phenyl which is unsubstituted or substituted,
$R^2$ is $(C_1-C_6)$alkyl, $(C_3-C_6)$cycloalkyl or phenyl, each of the 3 last-mentioned radicals is unsubstituted or substituted,
$R^3$ is hydrogen or a hydrocarbon radical having 1 to 18 C atoms which is unsubstituted or substituted. A method for controlling weeds, including applying to a plant, plant part, or locus thereof, an effective amount of the herbicidal composition. A method for imparting hydrolysis resistance to a herbicidal composition containing rimsulfuron by adding to the composition an effective amount of the compound of formula (I).

8 Claims, No Drawings

PROCESS FOR PREPARING A NOVEL FORMULATION OF RIMSULFURON AND USE OF THE SAME

BACKGROUND

Field of the Invention

The present invention relates to a novel formulation of 1-(4,6-dimethoxypyrimidin-2-yl)-3-(3-ethylsulfonyl-2-pyridylsulfonyl)urea (rimsulfuron) with an anti-hydrolysis agent, to processes for its preparation and to its use in agrochemical preparations.

Description of Related Art 1-(4,6-dimethoxypyrimidin-2-yl)-3-(3-ethylsulfonyl-2-pyridylsulfonyl)urea (Rimsulfuron) is a potent herbicide having high selectivity, high efficiency, low toxicity, and other desirably attributes. Rimsulfuron has a molecular formula of $C_{14}H_{17}N_5O_7S_2$. Its chemical structure is:

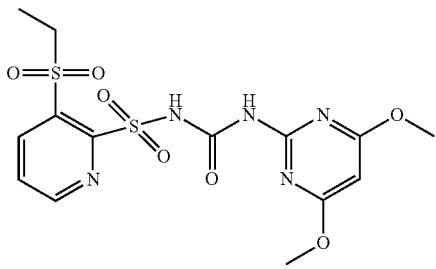

It is used post-emergence on crops, such as maize and potatoes, against a variety of annual and perennial grasses and broadleaved weeds. As may be expected for a selective herbicide, rimsulfuron can be highly toxic to some non-target plants, including duckweed, but it is rather less toxic towards algae and is of generally low toxicity towards most other wildlife.

Rimsulfuron, like other agricultural chemicals, can be formulated as concentrates in a variety of different formulations. However, when it is dissolved and dispersed in water, rimsulfuron can undergo significant hydrolysis. Furthermore, hydrolysis can occur during storage, particularly where the compound becomes exposed to moisture. As a result, the stability of rimsulfuron is of great concern.

U.S. Pat. No. 5,516,750, which is incorporated herein by reference for all purposes, describes the use of substituted isoxazolines as safeners to reduce phytotoxicity to plants for classes of pesticides, especially for post-emergent (tankmix) application of a safener-herbicide combination to the area under cultivation. The use of substituted isoxazolines as anti-hydrolysis agent has not been mentioned and exemplified.

SUMMARY

It has been found that making proper selection of a formulation adjuvant surprisingly helps to stabilize the active ingredient in the formulation. More particularly, it was surprisingly found that isoxazoline carboxylates can significantly inhibit the hydrolysis of rimsulfuron when the formulation is dissolved in water and/or stored for a period of time. The present disclosure relates to embodiments of invention that provides a novel formulation of rimsulfuron that reduces or avoids the hydrolysis problems encountered with previous formulations.

Accordingly, in one embodiment, the present invention relates to a novel formulation of 1-(4,6-dimethoxypyrimidin-2-yl)-3-(3-ethylsulfonyl-2-pyridylsulfonyl)urea (rimsulfuron) with an anti-hydrolysis agent, to processes for its preparation, and to its use in agrochemical preparations.

Surprisingly, it has been found that compounds from the group of 2-isoxazoline-3-carboxylic acid derivatives having the formula (I) below can be used as an anti-hydrolysis agent for rimsulfuron.

In another embodiment, the invention relates to a method of increasing the stability of rimsulfuron by applying an effective amount of a compound of the formula (I) or a salt thereof,

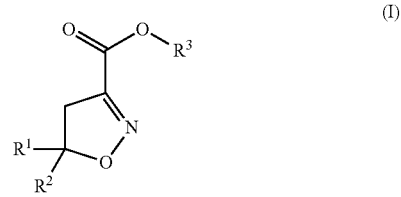

in which $R^1$ is phenyl which is unsubstituted or substituted, preferably unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and/or $(C_1-C_4)$alkylsulfonyl, $R^2$ is $(C_1-C_6)$alkyl, $(C_3-C_6)$cycloalkyl or phenyl, each of the 3 last-mentioned radicals is unsubstituted or substituted, preferably unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and/or $(C_1-C_4)$alkylsulfonyl, $R^3$ is hydrogen or a hydrocarbon radical having 1 to 18 C atoms which is unsubstituted or substituted, preferably unsubstituted or substituted by one or more radicals selected from the group consisting of halogen, cyano, thio, nitro, hydroxyl, $(C_1-C_6)$alkyl, $(C_1-C_6)$haloalkyl, the 2 last-mentioned radicals as substituents of cyclic radicals only, $(C_1-C_6)$alkoxy, $(C_2-C_6)$alkenyloxy, $(C_2-C_6)$alkinyloxy, $(C_1-C_6)$haloalkoxy, $(C_2-C_6)$alkylthio, $(C3-C_6)$cycloalkyl, $(C_3-C_6)$cycloalkoxy, $(C_1-C_8)$alkoxy carbonyl, $(C_2-C_6)$alkenyloxy-carbonyl, $(C_2-C_6)$alkinyloxy-carbonyl, $(C_1-C_8)$alkyl-carbonyl, $(C_1-C_6)$alkyl-carbonyloxy, phenyl, phenyl-$(C_1-C_6)$alkoxy, phenyl-$(C_1-C_6)$alkoxy-carbonyl, phenoxy, phenoxy-$(C_1-C_6)$alkoxy, phenoxy-$(C_1-C_6)$alkoxy-carbonyl, phenoxycarbonyl, phenylcarbonyloxy and phenyl-$(C_1-C_6)$alkyl-carbonyloxy, to a composition containing rimsulfuron.

Of particular interest are anti-hydrolysis compounds of the formula (I) or salts thereof in which $R^1$ and $R^2$ both are phenyl.

Preferably, the anti-hydrolysis compounds of formula (I) is ethyl 4,5-dihydro-5,5-diphenyl-1,2-oxazole-3-carboxylate (also known as isoxadifen or isoxadifen-ethyl).

The weight ratio of the anti-hydrolysis compounds to rimsulfuron varies within wide limits and is preferably in a range of about 1:10 to about 10:1, in particular in a range of about 1:10 to about 5:1.

The amount of rimsulfuron in the formulation can be less than about 50% by weight of the formulation, preferably less than about 30% by weight of the formulation, particularly preferably about 25% by weight of the formulation.

The herbicidal activity of rimsulfuron is known in the art and is used in commercial scale. Methods to formulate and use rimsulfuron-containing compositions are also known in the art. The formulations of rimsulfuron described herein according to embodiments of the present invention may be formulated and applied in an analogous manner.

In a further aspect, the present invention provides a herbicidal composition comprising rimsulfuron and an anti-hydrolysis agent as hereinbefore defined.

In another aspect, the invention furthermore provides processes for preparing compositions for controlling weeds comprising rimsulfuron and an anti-hydrolysis agent, and to methods for controlling weeds by applying a composition according to an embodiment of the invention.

In another embodiment, the invention provides a method for imparting hydrolysis resistance to a herbicidal composition comprising a herbicidally effective amount of rimsulfuron, comprising adding to the herbicidal composition a hydrolysis resistance providing effective amount of one or more 2-isoxazoline-3-carboxylic acid derivatives having formula (I):

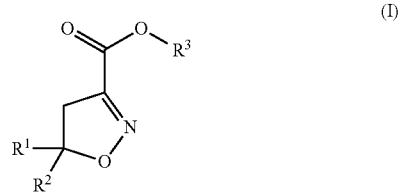

wherein
$R^1$ is phenyl which is unsubstituted or substituted, preferably unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and/or $(C_1-C_4)$alkylsulfonyl, $R^2$ is $(C_1-C_6)$alkyl, $(C_3-C_6)$cycloalkyl or phenyl, each of the 3 last-mentioned radicals is unsubstituted or substituted, preferably unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and/or $(C_1-C_4)$alkylsulfonyl, $R^3$ is hydrogen or a hydrocarbon radical having 1 to 18 C atoms which is unsubstituted or substituted, preferably unsubstituted or substituted by one or more radicals selected from the group consisting of halogen, cyano, thio, nitro, hydroxyl, $(C_1-C_6)$alkyl, $(C_1-C_6)$haloalkyl, the 2 last-mentioned radicals as substituents of cyclic radicals only, $(C_1-C_6)$alkoxy, $(C_2-C_6)$alkenyloxy, $(C_2-C_6)$alkinyloxy, $(C_1-C_6)$haloalkoxy, $(C_2-C_6)$alkylthio, $(C_3-C_6)$cycloalkyl, $(C_3-C_6)$cycloalkoxy, $(C_1-C_8)$alkoxy carbonyl, $(C_2-C_6)$alkenyloxy-carbonyl, $(C_2-C_6)$alkinyloxy-carbonyl, $(C_1-C_8)$alkyl-carbonyl, $(C_1-C_6)$alkyl-carbonyloxy, phenyl, phenyl-$(C_1-C_6)$alkoxy, phenyl-$(C_1-C_6)$alkoxy-carbonyl, phenoxy, phenoxy-$(C_1-C_6)$alkoxy, phenoxy-$(C_1-C_6)$alkoxy-carbonyl, phenoxycarbonyl, phenylcarbonyloxy and phenyl-$(C_1-C_6)$alkyl-carbonyloxy, In a particular embodiment, the hydrolysis resistance providing effective amount is from about 4 wt % to about 40 wt %, based upon the weight of the herbicidal composition.

In another particular embodiment, the hydrolysis resistance providing effective amount is from about 8 wt % to about 40 wt %, based upon the weight of the herbicidal composition.

In another particular embodiment, the hydrolysis resistance providing effective amount is from about 10 wt % to about 40 wt %, based upon the weight of the herbicidal composition.

DETAILED DESCRIPTION OF SPECIFIC EMBODIMENTS

The composition of rimsulfuron and anti-hydrolysis agent can be converted in a known manner to the customary formulations, such as suspension concentrates (SC), oil-based suspension concentrates (OD), soluble granules (SG), dispersible concentrates (DC), emulsifiable concentrates (EC), emulsion for seed treatment (ES), flowable concentrate for seed treatment (FS), granules, microgranules (MG), suspo-emulsions (SE), and water dispersible granules (WG), using suitable auxiliaries and carriers or solvents.

Here, rimsulfuron should be present in a concentration of from about 0.1% to about 50% by weight of the composition or formulation, i.e., in an amount sufficient to achieve the required dosage upon application to a locus where herbicidal control is desired. The formulations are prepared, for example, by combining rimsulfuron and the anti-hydrolysis agent with water, solvents and/or carriers, using, if appropriate, emulsifiers and/or dispersants, and/or other auxiliaries.

The formulations according to embodiments of the invention can be prepared by mixing rimsulfuron and the 2-isoxazoline-3-carboxylic acid anti-hydrolysis agent with herbicidally acceptable additives, for example, liquid diluents, solid diluents, wetting agents, dispersants, thickening agent and other formulation ingredients.

Liquid diluents include, for example, water, N,N-dimethylmamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut; ketones, such as cyclohexanone, 2-heptanone, isophorone and 4-hydroxy-4-methyl-2-pentanone; acetates, such as hexyl acetate, heptyl acetate and octyl acetate; and alcohols, such methanol, cyclohexanol, decanol, benzyl alcohol, and tetrahydrofurfuryl alcohol.

Solid diluents can be water-soluble or water-insoluble. Water-soluble solid diluents include, but are not limited to, salts, such as alkali metal phosphates (e.g., sodium dihydrogen phosphate), alkaline earth phosphates, sulfates of sodium, potassium, magnesium and zinc, sodium and potassium chloride, sodium acetate, sodium carbonate, sodium benzoate, and/or sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum oxide, calcium oxide, and zinc oxide.

Wetting agents include, but are not limited to, alkyl sulfosuccinates, laureates, alkyl sulfate and phosphate esters, acetylenic diols, ethoxyfluorinated alcohols, ethoxylated silicones, alkyl phenol ethyloxylates, benzene sulfonates, alkyl-substituted benzene sulfonates, alkyl α-olefin sulfonates, naphthalene sulfonates, alkyl-substituted naphthalene sulfonates, condensates of naphthalene sulfonates and alkyl-substituted naphthalene sulfonates with formaldehyde, and alcohol ethoxylates, and salt forms of any of these. Alkyl naphthalene sulfonate, sodium salt is particularly preferred for the composition and formulation of the invention.

Dispersants include, but are not limited to, sodium, calcium and ammonium salts of lignosulfonates (optionally polyethoxylated); sodium and ammonium salts of maleic anhydride copolymers; sodium and ammonium salts of condensed phenolsulfonic acid; and naphthalene sulfonate-formaldehyde condensates and their sodium and ammonium salts. Of note are compositions comprising up to about 10% by weight of dispersant. Lignosulfonates, such as sodium lignosulfonates, are particularly preferred for the composition and formulation of the invention. Naphthalene sulfonate-formaldehyde condensates (and salts thereof), such as condensation products of naphthalenesulfonic acid polymer with formaldehyde, sodium salt are particularly preferred for the composition and formulation of the invention.

Thickeners include, but are not limited to, guar gum, pectin, casein, carrageenan, xanthan gum, alginates, methylcellulose, hydroxyethylcellulose, hydroxypropylcellulose and carboxymethylcellulose. Synthetic thickeners include derivatives of the former categories, and also polyvinyl alcohols, polyacrylamides, polyvinylpyrrolidones, polyethers and their copolymers as well as polyacrylic acids and their salts. Alkylpolyvinylpyrrolidone is particularly preferred for the composition and formulation of embodiments of the invention.

Other formulation ingredients can be used in certain embodiments of the present invention, such as dyes, defoamers, drying agents, and the like. These formulation ingredients are known to one skilled in the art.

The rimsulfuron forming a component of formulations according to embodiments of the invention can be present in its commercially available formulations and use forms, prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals, and combinations thereof). A mixture with other known active compounds (such as herbicides, fertilizers, growth regulators, safeners, semiochemicals, or with agents for improving plant properties) is also possible.

When used as herbicide according to embodiments of the invention, the active compound can be present in their commercially available formulations and use forms, in a form prepared from these formulations, or as a mixture with synergistic agents. Synergistic agents are compounds which increase the action of the active compounds, without it being necessary for the synergistic agent added to be active itself.

Any plants or plant parts susceptible to control or protection by rimsulfuron can be treated in accordance with embodiments of the invention. Plants are to be understood as meaning in the present context all plants and plant populations, such as desired and undesired wild plants or crop plants (including naturally occurring crop plants). Crop plants can be plants which can be obtained by conventional breeding and optimization methods, by biotechnological and genetic engineering methods, or by combinations of these methods including the transgenic plants and the plant cultivars which may or may not be protected by plant breeders' rights. Plant parts are to be understood as meaning all parts and organs of plants either above or below the ground, such as shoot, leaf, flower and root. Examples of which may be mentioned include leaves, needles, stalks, stems, flowers, fruit bodies, fruits, seeds, roots, tubers and rhizomes. The plant parts also include harvested material, and vegetative and generative propagation material such as cuttings, tubers, rhizomes, offshoots and seeds.

Treatment according to an embodiment of the invention of the plants and plant parts with the active compounds is carried out directly (i.e., by direct application of the formulation to the plants or plant parts) or by applying the compounds to the surroundings, habitat, or storage space of the plants or plant parts, also known as application to the locus of the plants or plant parts. Examples of such application methods include dipping, spraying, vaporizing, fogging, broadcasting, painting on, and in the case of propagation material, applying one or more coats, particularly in the case of seed.

The invention may be used to control dicotyledonous weeds such as *Abutilon* spp., *Ambrosia* spp., *Amaranthus* spp., *Chenopodium* spp., *Erysimum* spp., *Euphorbia* spp., *Fallopia* spp., *Galium* spp., *Hydrocotyle* spp., *Ipomoea* spp., *Lamium* spp., *Medicago* spp., *Oxalis* spp., *Plantago* spp., *Polygonum* spp., *Richardia* spp., *Sida* spp., *Sinapis* spp., *Solarium* spp., *Stellaria* spp., *Taraxacum* spp., *Trifolium* spp., *Veronica* spp., *Viola* spp. and *Xanthium* spp.

The invention may also be used to control monocotyledonous weeds such as *Agrostis* spp., *Alopecurus* spp., *Apera* spp., *Avena* spp., *Brachiaria* spp., *Bromus* spp., *Digitaria* spp., *Echinochloa* spp., *Eleusine* spp., *Eriochloa* spp., *Leptochloa* spp., *Lolium* spp., *Ottochloa* spp., *Panicum* spp., *Paspalum* spp., *Phalaris* spp., *Poa* spp., *Rottboellia* spp., *Setaria* spp., *Sorghum* spp., both intrinsically sensitive as well as resistant (e.g. ACCase and/or ALS resistant) biotypes of any of these grass weeds, as well as broadleaf monocotyledonous weeds such as *Commelina* spp., *Monochoria* spp., *Sagittaria* spp. and sedges such as *Cyperus* spp. and *Scirpus* spp.

The benefits of embodiments of the present invention are most noticeable when the pesticidal composition and/or formulation is applied to kill weeds in growing crops of useful plants: such as maize (corn) including field corn, popcorn and sweet corn; cotton, wheat, rice, oats, potato sugarbeet, plantation crops (such as bananas, fruit trees, rubber trees, tree nurseries), vines, asparagus, bushberries (such as blueberries), cranberries, cranberries, flax, grain *sorghum*, okra, peppermint, rhubarb, spearmint and sugarcane. Treatment of growing crops of maize and potatoes are particularly beneficial.

As used herein, the word "about" when used in connection with a numerical amount or range, means somewhat more or somewhat less than the stated numerical amount or range, to a deviation of ±10% of the stated numerical amount or endpoint of the range.

"Locus" and "surrounding," as used herein, refers to the place on which the plants are growing, the place on which the plant propagation materials of the plants are sown or the place on which the plant propagation materials of the plants will be sown.

All percentages are given in weight % unless otherwise indicated.

Embodiments of the present invention will now be described by the following examples which are provided for illustrative purposes only, and not intended to limit the scope of the disclosure.

EXAMPLES

Examples 1, 3-8, 10, and 12 describe the preparation of compositions of embodiments of the present invention. Comparative Examples 2, 11, and 13 describe the preparation of a corresponding composition lacking anti-hydrolysis agent. Examples 9 and 14 describe the stability testing of the above Examples and Comparative Examples and compare the results of that testing.

The stability of the rimsulfuron in these compositions was determined by aging samples in heated ovens having the same atmosphere therein, and then comparing the rimsulfuron content before and after aging to determine relative percentage of hydrolysis (RPH). RPH was calculated by the following equation:

$$RPH = \frac{\left(\begin{array}{c}\text{The final weight \% of rimsulfuron}-\\ \text{The initial weight \% of rimsulfuron}\end{array}\right)}{\text{The initial weight \% of rimsulfuron}} \times 100\%$$

Rimsulfuron content was determined by assaying the compositions with high-pressure liquid chromatography (HPLC) using reverse phase columns and eluants.

Example 1

Preparation of OD Formulation

All the components list in Table 1 below were mixed uniformly and the resulting mixture was ground with a Dyno-Mill (manufactured by Willy A. Bachofen AG) to obtain an oil-based suspension concentrate.

TABLE 1

| Ingredients | Weights % | Function |
|---|---|---|
| Rimsulfuron, 98% | 40.8 | Active compound |
| Isoxadifen-ethyl, 98% | 10.2 | Anti-hydrolysis agent |
| Sodium lignosulfonate (REAX 88B ®) | 14 | Dispersing agent |
| Alkylpolyvinylpyrrolidone | 10 | Thickening agent |
| Corn oil | Balance to 100% | Carrier |

Comparative Example 2 and Examples 3-8

Preparation of OD Formulations

Comparative Example 2 and Examples 3-8 were prepared by mixing the components in Table 2 to obtain a uniform mixture and the resulting mixture was ground with a Dyno-Mill (manufactured by Willy A. Bachofen AG) to obtain an oil-based suspension concentrate.

TABLE 2

| Content | Comparative Example 2 | Example 3 | Example 4 | Example 5 | Example 6 | Example 7 | Example 8 |
|---|---|---|---|---|---|---|---|
| Rimsulfuron, 98% | 40.8% | 40.8% | 40.8% | 20.4% | 10.2% | 8.16% | 4.08% |
| Isoxadifen-ethyl, 98% | 0% | 4.08% | 8.16% | 20.4% | 20.4% | 40.8% | 40.8% |
| Sodium lignosulfonate (REAX 88B ®) | 22% | 14% | 14% | 14% | 14% | 14% | 14% |
| Alkylpolyvinylpyrrolidone | 20% | 10% | 10% | 10% | 10% | 10% | 10% |
| Corn oil | Balance to 100% | Balance to 100% | Balance to 100% | Balance to 100% | Balance to 100% | Balance to 100% | Balance to 100% |

Example 9

Stability Test

The samples (from Examples 1-8 and from Comparative Example 2) were bottled and then aged in an oven at 54° C. for 1 and 2 weeks. The content of rimsulfuron was determined by HPLC. The results are given in Tables 3 and 4.

TABLE 3

Stability of rimsulfuron (1 week)

| Sample | Weight % of rimsulfuron | RPH |
|---|---|---|
| Example 1 | 40 | 0 |
| Comparative Example 2 | 40 | −50 |
| Example 3 | 40 | −1 |
| Example 4 | 40 | −0.5 |
| Example 5 | 20 | 0 |
| Example 6 | 10 | 0 |
| Example 7 | 8 | −0.5 |
| Example 8 | 4 | −1 |

TABLE 4

Stability of rimsulfuron (2 weeks)

| Sample | Weight % of Rimsulfuron | RPH |
|---|---|---|
| Example 1 | 40 | 0 |
| Comparative Example 2 | 40 | −70 |
| Example 3 | 40 | −2 |
| Example 4 | 40 | −1 |
| Example 5 | 20 | 0 |
| Example 6 | 10 | 0 |
| Example 7 | 8 | −1 |
| Example 8 | 4 | −2 |

These results show that compositions according to embodiments of the invention exhibit only minimal hydrolysis of rimsulfuron when amounts of isoxadifen-ethyl are included ranging from about 4 to about 40 wt %. Such a result is surprising and unexpected.

Example 10

Preparation of SG Formulation

All the components list in Table 5 below were mixed together. The mixture was blended and milled in a high-speed rotary mill. Water was added to the mixture to obtain an extrudable paste. The paste was extruded through a die or screen to form extrudate. The extrudate was dried at 70° C. in a vacuum oven and then sifted through 0.71-2 mm screens to obtain granules.

TABLE 5

| Ingredients | Weights % | Function |
| --- | --- | --- |
| Rimsulfuron, 98% | 25.51 | Active compound |
| Isoxadifen-ethyl, 98% | 5.1 | Anti-hydrolysis agent |
| Lignosulfonic acid, sodium salt, (REAX 88B ®) | 15 | Dispersing agent |
| Naphthalenesulfonic acid, polymer with formaldehyde, sodium salt (TOMAL ® NN8906) | 6 | Dispersing agent |
| Sodium acetate | 4 | Filler |
| Sodium carbonate | 4 | Filler |
| Non-ionic aqueous emulsion of polydimethylsiloxanes | 1 | Antifoam agent |
| Mannitol | Balance to 100% | Carrier |

Comparative Example 11

Preparation of SG Formulation

All the components list in Table 6 below were mixed together. The mixture was blended and milled in a high-speed rotary mill. Water was added to the mixture to obtain an extrudable paste. The paste was extruded through a die or screen to form extrudate. The extrudate was dried at 70° C. in a vacuum oven and then sifted through 0.71-2 mm screens to obtain granules.

TABLE 6

| Ingredients | Weights % | Function |
| --- | --- | --- |
| Rimsulfuron, 98% | 25.51 | Active compound |
| Isoxadifen-ethyl, 98% | 0 | Anti-hydrolysis agent |
| Lignosulfonic acid, sodium salt, (REAX ® 88B) | 15 | Dispersing agent |
| Naphthalenesulfonic acid, polymer with formaldehyde, sodium salt (TOMAL ® NN8906) | 6 | Dispersing agent |
| Sodium acetate | 4 | Filler |
| Sodium carbonate | 4 | Filler |
| Non-ionic aqueous emulsion of polydimethylsiloxanes | 1 | Antifoam agent |
| Mannitol | Balance to 100% | Carrier |

Example 12

Preparation of WDG Formulation

All the components list in Table 7 below were mixed together. The mixture was blended and milled in a high-speed rotary mill. Water was added to the mixture to obtain an extrudable paste. The paste was extruded through a die or screen to form extrudate. The extrudate was dried at 70° C. in a vacuum oven and then sifted through 0.71-2 mm screens to obtain granules.

TABLE 7

| Ingredients | Weights % | Function |
| --- | --- | --- |
| Rimsulfuron, 98% | 25.51 | Active compound |
| Isoxadifen-ethyl, 98% | 5.1 | Anti-hydrolysis agent |
| Alkyl naphthalene sulphonate, sodium salt (Akzo Nobel) | 2 | Wetting agent |
| Lignosulfonic acid, sodium salt, (REAX ® 88B) | 15 | Dispersing agent |
| Naphthalenesulfonic acid, polymer with formaldehyde, sodium salt (TOMAL ® NN8906) | 6 | Dispersing agent |
| Sucrose | 10 | Filler |
| Non-ionic aqueous emulsion of polydimethylsiloxanes | 1 | Antifoam agent |
| Mannitol | Balance to 100% | Carrier |

Comparative Example 13

Preparation of WDG Formulation

All the components list in Table 8 below were mixed together. The mixture was blended and milled in a high-speed rotary mill. Water was added to the mixture to obtain an extrudable paste. The paste was extruded through a die or screen to form extrudate. The extrudate was dried at 70° C. in a vacuum oven and then sifted through 0.71-2 mm screens to obtain granules.

TABLE 8

| Ingredients | Weights % | Function |
| --- | --- | --- |
| Rimsulfuron, 98% | 25.51 | Active compound |
| Isoxadifen-ethyl, 98% | 0 | Anti-hydrolysis agent |
| Alkyl naphthalene sulphonate, sodium salt (Akzo Nobel) | 2 | Wetting agent |
| Lignosulfonic acid, sodium salt, (REAX ® 88B) | 15 | Dispersing agent |
| Naphthalenesulfonic acid, polymer with formaldehyde, sodium salt (TOMAL ® NN8906) | 6 | Dispersing agent |
| Sucrose | 10 | Filler |
| Non-ionic aqueous emulsion of polydimethylsiloxanes | 1 | Antifoam agent |
| Mannitol | Balance to 100% | Carrier |

Examples 14

Stability Test

The samples (from Examples 10 and 12 and Comparative Examples 11 and 13) were bottled and aged in an oven at 54° C. for 1 week, and then the content of rimsulfuron was determined. Stability results are listed in Table 9.

TABLE 9

| Stability of rimsulfuron (1 week) | | |
| --- | --- | --- |
| Sample | Weight % of Rimsulfuron | RPH |
| Example 10 | 25 | 0 |
| Comparative Example 11 | 25 | −30 |
| Example 12 | 25 | 0 |
| Comparative Example 13 | 25 | −40 |

It can be seen from these results that the inclusion of the anti-hydrolysis agent provides excellent protection to the rimsulfuron against hydrolysis as compared to compositions where the anti-hydrolysis agent is not included. Such a result is surprising and unexpected.

The invention claimed is:

1. A herbicidal composition comprising:
a herbicide consisting essentially of rimsulfuron in an amount of between 20.4% and 40.8% by weight of the composition, and
a hydrolysis inhibiting effective amount of an anti-hydrolysis agent, which comprises one or more 2-isoxazoline-3-carboxylic acid derivatives having a formula (I):

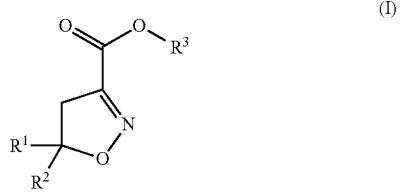

wherein
$R^1$ is phenyl which is unsubstituted or substituted by one or more radicals selected from the group consisting of halogen, cyano, nitro, amino, $(C_1$-$C_4)$haloalkyl, $(C_1$-$C_4)$haloalkoxy, $(C_1$-$C_4)$alkyl, $(C_1$-$C_4)$alkoxy, mono$(C_1$-$C_4)$alkyl-amino, di$(C_1$-$C_4)$alkyl-amino, $(C_1$-$C_4)$alkylthio and/or $(C_1$-$C_4)$alkylsulfonyl,
$R^2$ is $(C_1$-$C_6)$alkyl, $(C_3$-$C_6)$cycloalkyl or phenyl, each of the 3 last-mentioned radicals is unsubstituted or substituted by one or more radicals selected from the group consisting of halogen, cyano, nitro, amino, $(C_1$-$C_4)$haloalkyl, $(C_1$-$C_4)$haloalkoxy, $(C_1$-$C_4)$alkyl, $(C_1$-$C_4)$alkoxy, mono$(C_1$-$C_4)$alkyl-amino, di$(C_1$-$C_4)$alkyl-amino, $(C_1$-$C_4)$alkylthio and/or $(C_1$-$C_4)$alkylsulfonyl,
$R^3$ is hydrogen or a hydrocarbon radical having 1 to 18 C atoms which is unsubstituted or substituted by one or more radicals of $(C_1$-$C_6)$alkyl,
wherein an amount of the antihydrolysis agent is between 4.08% and 20.4% by weight of the composition and the amount of antihydrolysis agent to the amount of rimsulfuron is in a range of about 10:1 to about 1:10, and
whereby the antihydrolysis agent in the composition protects the rimsulfuron from water and moisture in the composition and inhibits the hydrolysis of the rimsulfuron in the composition and maintains the stability of the rimsulfuron in the composition.

2. The herbicidal composition according to claim 1, wherein the anti-hydrolysis agent is isoxadifen-ethyl.

3. The herbicidal composition according to claim 1, wherein the composition is formulated as a suspension concentrate (SC), an oil-based suspension concentrate (OD), a soluble granule (SG), a dispersible concentrate (DC), an emulsifiable concentrate (EC), an emulsion for seed treatment (ES), a flowable concentrate for seed treatment (FS), a granule, a microgranule (MG), a suspo-emulsion (SE), or a water dispersible granule (WG).

4. The herbicidal composition according to claim 3, further comprising one or more auxiliaries selected from the group consisting of a liquid diluent, a solid diluent, a wetting agent, a dispersant, a thickening agent, and combinations thereof.

5. A method for controlling weeds, comprising applying to a plant or plant part, or the surroundings thereof, an effective amount of the herbicidal composition according to claim 1.

6. A method for imparting hydrolysis resistance to a herbicidal composition comprising: providing a herbicide consisting essentially of rimsulfuron in an amount of between 20.4% and 40.8% by weight of the composition, comprising adding to the herbicidal composition a hydrolysis resistance agent of one or more 2-isoxazoline-3-carboxylic acid derivatives having a formula (I)

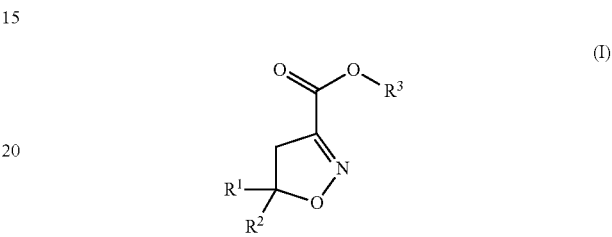

wherein
$R^1$ is phenyl which is unsubstituted or substituted by one or more radicals selected from the group consisting of halogen, cyano, nitro, amino, $(C_1$-$C_4)$haloalkyl, $(C_1$-$C_4)$haloalkoxy, $(C_1$-$C_4)$alkoxy, mono$(C_1$-$C_4)$alkyl-amino, di$(C_1$-$C_4)$alkyl-amino, $(C_1$-$C_4)$alkylthio and/or $(C_1$-$C_4)$alkylsulfonyl,
$R^2$ is $(C_1$-$C_6)$alkyl, $(C_3$-$C_6)$cycloalkyl or phenyl, each of the 3 last-mentioned radicals is unsubstituted or substituted by one or more radicals selected from the group consisting of halogen, cyano, nitro, amino, $(C_1$-$C_4)$haloalkyl, $(C_1$-$C_4)$haloalkoxy, $(C_1$-$C_4)$alkyl, $(C_1$-$C_4)$alkoxy, mono$(C_1$-$C_4)$alkyl-amino, di$(C_1$-$C_4)$alkyl-amino, $(C_1$-$C_4)$alkylthio and/or $(C_1$-$C_4)$alkylsulfonyl,
$R^3$ is hydrogen or a hydrocarbon radical having 1 to 18 C atoms which is unsubstituted or substituted by one or more radicals $(C_1$-$C_6)$alkyl,
wherein the hydrolysis resistance agent is between 4.08% and 20.4% by weight of the composition and the hydrolysis resistance agent agent to the rimsulfruon is in a range of about 10:1to about 1:10, and
whereby the hydrolysis agent resistance agent in the composition protects the rimsulfuron from water and moisture in the composition and inhibits the hydrolysis of the rimsulfuron in the composition and maintains the stability of the rimsulfuron in the composition.

7. The method according to claim 6, wherein the hydrolysis resistance providing effective amount is at least about 8 wt % based upon the weight of the herbicidal composition.

8. The method according to claim 7, wherein the hydrolysis resistance providing effective amount is at least about 10 wt % based upon the weight of the herbicidal composition.

* * * * *